United States Patent [19]

Wagner

[11] 4,144,569
[45] Mar. 13, 1979

[54] METHOD AND ARRANGEMENT FOR COMPENSATING MOTION ARTIFACTS IN COMPUTED TOMOGRAPHY

[75] Inventor: Wolfgang Wagner, Norderstedt, Fed. Rep. of Germany

[73] Assignee: U.S. Philips Corporation, New York, N.Y.

[21] Appl. No.: 839,620

[22] Filed: Oct. 5, 1977

[30] Foreign Application Priority Data

Oct. 8, 1976 [DE] Fed. Rep. of Germany ....... 2645416

[51] Int. Cl.$^2$ ............................................ G01N 23/00
[52] U.S. Cl. ................................. 364/414; 250/445 T
[58] Field of Search .................... 364/414; 250/445 T, 250/366, 369

[56] References Cited

U.S. PATENT DOCUMENTS

| | | | |
|---|---|---|---|
| 3,778,614 | 12/1973 | Hounsfield | 250/445 T X |
| 3,961,186 | 6/1976 | Leunbach | 250/445 T X |
| 3,971,948 | 7/1976 | Pfeiler et al. | 250/445 T |
| 4,002,911 | 1/1977 | Hounsfield | 250/445 T X |
| 4,010,371 | 3/1977 | LeMay | 250/445 T X |
| 4,063,074 | 12/1977 | Wagner | 364/414 |
| 4,066,903 | 1/1978 | LeMay | 250/445 T X |
| 4,070,707 | 1/1978 | Barber | 364/414 |

*Primary Examiner*—Edward J. Wise
*Attorney, Agent, or Firm*—Thomas A. Briody; Jack E. Haken

[57] ABSTRACT

Artifacts may be produced when a body moves relative to a CT scanner during measurement. Such artifacts are avoided by shifting the measuring values relative to their coordinates as though they were obtained from a non-moving body. The weighted-mean point is determined for each series of measuring values for each specific orientation of the measuring beams. The distance to a point of the image plane is subsequently determined for all weighted-mean lines which pass through said weighted-mean point perpendicular to the measuring coordinates. Next, the measuring values are then shifted or processed in a shifted manner in conformity with said distance.

3 Claims, 5 Drawing Figures

METHOD AND ARRANGEMENT FOR COMPENSATING MOTION ARTIFACTS IN COMPUTED TOMOGRAPHY

The invention relates to a method of determining the spatial distribution of the absorption of radiation in a planar slice of a body from a plurality of measuring sets, which each represent a series of measuring values which corresponding to an integral of the absorption of the body along one of a multiplicity of at least substantially parallel measuring beams, the various measuring sets being derived from measuring values obtained with the aid of measuring beams which are differently oriented relative to each other within the planar slice and the spatial distribution of the absorption being derived from the sets of measuring values by superposition. The invention also relates to an arrangement for carrying out said method.

Such a method is known from German DT-OS 19 41 443, laid open to public inspection. In accordance with this method the measuring values of one series, i.e. the measuring values of all measuring beams with different orientations are recorded time-sequentially. The spatial distribution of the absorption is then reconstructed by superposition by means of a mathematical algorithm.

However, a disadvantage of this manner of recording the measuring values is that translational movements of the body during the measurement lead to annoying image errors which render the interpretation of the absorption distribution difficult or even impossible. The image errors appear as streaked artifacts issuing from those areas in the planar slice of the body in which the absorption varies substantially. The intensity of these streaks depends both on the intensity and variation in time of the movement and on the absorption differences in the said areas.

In order to reduce such motional errors, it is known from German DT-OS 25 06 686, laid open to public inspection, not only to rotate the measuring beams consecutively through a 180° angle, which is at least necessary for the complete reconstruction, but through a larger angle, and to employ the mean values for the measuring values obtained by measuring beams which make an angle of 180° with each other, i.e. which are oriented opposite to each other. In this respect it is assumed that a substantial part of the motional image-errors are caused by different positions of the body at the beginning and the end of the measurement. However, by this method the image-errors caused by movement of the body are not eliminated, but merely spread over a larger area of the planar slice, so that they appear less distinct in the reconstructed absorption distribution. Moreover, this method does not allow for other motional image-errors which cannot be attributed to positional differences at the beginning and at the end of the measurement, but to movements of the body during the intermediate orientations. Further disadvantages are the increased radiation dose administered to a patient when the absorption distribution of X-rays in a human body is measured, which is necessarily caused by measurement over an additional angular range, as well as the prolonged duration of the measuring process, which increases the likelihood of further movements of the body.

It is an object of the invention to provide a method by which the effects of movement of the body during the measurement are substantially compensated for. The method according to the invention solves this problem and is characterized in that, for each measuring set the weighted-mean point $(S\beta)$ is determined and for the weighted-mean line $(G\beta)$, which is a straight line passing through the weighted-mean point of each measuring set parallel to the measuring beams of said set, the perpendicular distance $(D(G\beta, B))$ to an arbitrary point (B) of the planar slice is determined, which distance is to be referred to hereinafter as weighted-mean distance, and that the absorption distribution is determined by the superposition of the measuring values $(Q(p,\beta))$, which have been shifted by the weighted-mean distances of the corresponding measuring set.

In this way the movement of the body during the measurement is reconstructed from the measuring values, by means of the pattern of movement thus determined the allocation of the measuring values to the body coordinates, (i.e. to the measuring beams) is corrected, as through said values were measured on a non-moving body. Thus, the measuring values applied to the computing circuit for determining the absorption distribution are shifted by this amount or are in the shifted position respectively. Consequently, the measuring process itself and the geometrical set-up of the measuring arrangement remain the same.

If the position of the arbitrary point from to which the distances of the weighted-mean lines are determined is chosen unfavourably, weighted-mean distances may be obtained which at least partially shift the measuring values outside the image field wherein image reconstruction takes place. If, for each weighted-mean line the perpendicular distance to a probable weighted-mean point is determined, for which the sum of the weighted-mean distances of all weighted-mean lines is a minimum, the shifted measuring values will be situated within the image field.

Generally, a body will make no abrupt movements, during measurement but the movements will vary uniformly during several consecutive orientations of the measuring beams. Consequently, the measuring values of a measuring set which result from points of the body that are spaced from each other are then shifted by amounts which differ correspondingly. Thus, within a measuring set the measuring values may be effectively shifted by an amount which depends on the distance of the measuring beam which corresponds to the measuring value from the weighted-mean point of the measuring set and on the distance of the weighted-mean lines of the measuring sets which were measured immediately before and after the relevant set.

Owing to this different shift of the individual measuring values of a series it is possible, in particular in the case of intense movements, that the series of shifted measuring values, yields a weighted-mean point which differs from the weighted-mean point initially determined. Therefore it is effective if new weighted-mean points and new weighted-mean distances of the corresponding weighted-mean lines to said initially determined point are determined, and the measuring values are shifted again in accordance with these new weighted-mean distances. In this way the actual displacement of the body is approximated iteratively.

A device for carrying out the method in accordance with the invention comprises a radiator for generating a beam of a body penetrating radiation and one or more detectors for measuring the radiation passing through a planar slice of the body. The measurements are performed with radiation passing at different orientations through the planar slice of the body, the direction of the radiation always being in the plane of said slice. The device comprising further a memory for storing the series of measuring values and a first arithmetic unit for determining the spatial absorption distribution in the planar slice by superposition. A second arithmetic unit is provided and connected to the memory, which unit to determine the value of the coordinates of the weighted-mean point (S$\beta$) for each series of measuring values (Q(p,$\beta$)) measured with at least substantially the same orientation, using the relationship $$S\beta = \frac{\sum_p p \cdot Q(p,\beta)}{\sum_p Q(p,\beta)}.$$

The device further comprising a weighted-mean memory for storing the weighted-mean points, a third arithmetic unit for determining the value of the perpendicular weighted-mean distance (D(G$\beta$, B) from the line through the weighted-mean point to the coordinates (B$_x$, B$_y$) of a fixed point (B) for each weighted-mean point using the relationship $$\Delta S\beta = S\beta + B_x \sin\beta - B_y \cos\beta;$$

and a distance memory for storing the weighted-mean distances. The first arithmetic unit then determines the distribution of absorption in the planar slice using the measuring values of measuring series shifted by the appropriate weighted-mean distance.

The invention will now be described in more detail by way of example with reference to the drawing. In the drawing:

FIG. 5 shows a further part of the block diagram of FIG. 3 in more detail, In FIG. 1 is shown a diagnostic apparatus having an annular shaped frame 100 which can be rotated and has been placed on rolls 105 and 107. The apparatus comprises an X-ray source 3 and an X-ray detector 5 which are mounted on rails 101 and 103 respectively. The source 3 and detector 5 can be guided along the rails 101 and 103 to scan a planar slice of a body 10 with parallel X-ray measuring beams of which only one 4 is shown. To scan the body 10 in a large number of different direction after each lateral scanning movement of source 3 and detector 5 the frame 100 is rotated. The direction of the X-ray beam 4 is thus rotated relative to the X- and Y axes shown in the figure. The X- and Y axes together constitute a coordinate-system to be used when the absorption distribution is reconstructed. The radiator 3 emits an X-ray beam 4 which is measured by the detector 5, after the beam has been attenuated during passage through the body 10. The axis 2, which extends parallel to the measuring beam 4, and the axis 6 which is perpendicular thereto, represent a further coordinate system, which has a fixed relationship with the frame 100 and the arrangement of the radiator 3 and the detector 5 and which is rotated stepwise relative to the coordinate axes X, Y. In the arrangement shown the angle between the two coordinate systems is designated $\beta$, and this angle is referred to as the orientation of the measuring beam 4. For each orientation $\beta$ the arrangement of the radiator 3 and the detector 5 is shifted in parallel in the direction of the axis 6 and a series of measuring values each of which represents the integral of the absorption of the body 10 across each measuring beam with the same angle of orientation $\beta$ is recorded. Scanning of the body 10 is started at point 7 where the measuring beam 4 intersects the straight line 6 and scanning is terminated at point 8 where the measuring beam 4 intersects the straight line 6. In order to allow for tolerances in the size of the body 10, the measurement begins before the intersection 7 and is not terminated until after the intersection 8. All measuring values Q(p,$\beta$), where p represents the location relative to the axis 2 of the point of intersection of the measuring beam 4 and the axis 6 and the measuring values have been measured for a specific orientation $\beta$ corresponding to the angle between the two coordinate systems, are referred to as a series of measuring values. Further it is assumed that the measuring values have been converted logarithmically before storage, so that their logarithmic value equals the integral of the absorption in the strip which is defined by the measuring beam. Furthermore, each function represented a series of measuring values is filtered by a high-pass filter before storage.

Figure 1:
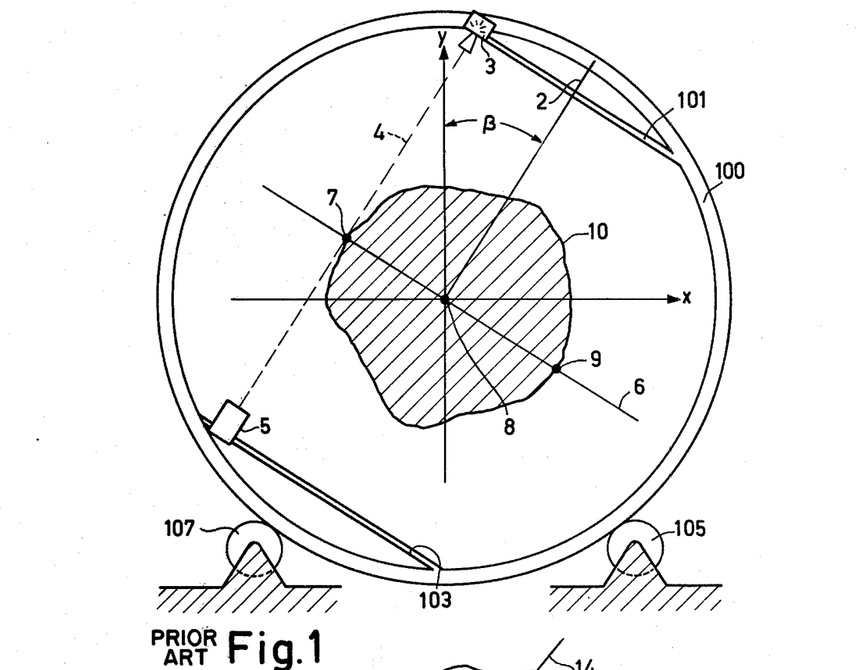
FIG. 1 illustrates the geometrical construction of prior art arrangement.

If the body 10 moves during the measurement, the position of the body relative to the reference system x-y changes and thus the location of the measuring values relative to the axes 2–6. In order to compensate for this movement in the measuring values, it suffices to shift the individual measuring values in respect of the location on the axis 6, i.e. only the component of the movement perpendicular to the direction of the measuring beam is allowed for.

The weighted-mean point of the body 10 is used to determine this movement component. If S$\beta$ is the weighted-mean point of a series of measuring values Q(p,$\beta$) and S$_x$ and S$_y$ are the weighted-mean coordinates of the spatial absorption function of the body 10, then the following relationship should be valid:

$$S\beta = S_y \cdot \cos\beta - S_x \cdot \sin\beta$$

This means that all weighted-mean lines G$\beta$, which pass through the weighted-mean point S$\beta$ with the orientation $\beta$ should intersect in one point, namely (S$_x$, S$_y$). Tests on phantoms, i.e. non-moving bodies, have revealed that even under the influence of noise errors, which are for example caused by the quantum nature of the radiation and by noise produced by the detectors and detector electronics, the above-mentioned relationship is satisfied with a slight deviation, which only amounts to fractions of one detector width. However, if the body has moved during the measurement, the weighted-mean lines G$\beta$ do not intersect in one point. If for each weighted-mean line G$\beta$ the weighted mean distance D(G$\beta$) to a fixed point B, which is situated substantially in the center of the planar slice, for example B = (0,0), is calculated, the weighted-mean point S$_x$, S$_y$ of the absorption function being unknown at this instant, i.e. $\Delta S\beta$ = D(G$\beta$, B), motional image errors can be avoided in that value $\Delta p = \Delta S\beta$ is added to the positions p,$\beta$ hence $$Q(p,\beta) = Q'(p + \Delta S\beta, \beta).$$

Figure 2:
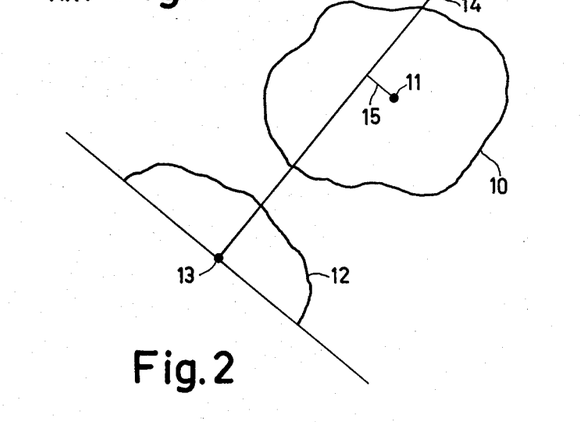
FIG. 2 is a schematic diagram to illustrate how the weighted-mean distance of the weighted-mean lines is determined.

This is illustrated in FIG. 2. In this Figure the body 10 is shown with its weighted-mean absorption point 11 in the original position, while owing to a movement of the body over the distance 15 a function 12 corresponding to a series of measuring values has a weighted-mean point in point 13. The weighted-mean line 14 through this weighted-mean point 13 then also has a perpendicular distance 15 from the original weighted-mean point 11 of the body 10. By shifting all measuring values of the function 12 over this distance 15 the weighted-mean point 13 then assumes such a position that the weighted-mean line 14 passes through the weighted-mean point 11 of the body 10, i.e. the measuring values are then situated as though they have been derived from a body which has not moved. This is also valid if the distance to an arbitrary point in the planar slice is determined, provided that this point is the same for all series of measuring values, instead of the distance to the unknown original weighted-mean absorption point of the body 10, because in the reconstructed spatial absorption distribution its weighted-mean point then coincides with this arbitrarily selected point.

As it may happen that in the case of an unfavourable choice of said point individual points of the reconstructed spatial absorption function are situated outside the image field, such a point in the planar slice may be selected which relative to all weighted-mean lines $G\beta$ is situated so that the sum of all $\Delta S\beta$ reaches a minimum value, i.e. that the required shift of the measuring values $Q(p + \Delta S\beta,\beta)$ is minimal. The x and y-components of this point may be calculated from $$B'_x = \frac{2\Delta\beta}{\pi} \sum_\beta S\beta \sin\beta$$
$$B'_y = \frac{2\Delta\beta}{\pi} \sum_\beta S\beta \cos\beta$$

where $\Delta\beta$ is the angular difference of the orientations between two successive measuring sets.

During the translation of the radiatordetector to radiator detector system there may also be movements, correction of the detector position $p$ is therefore not effected by means of a constant correction value $\Delta S\beta$, but by means of a varible value $\Delta S\beta(p)$, whose derivation is explained hereinafter A basic assumption for this is that the movement is smooth, i.e. that the movement changes only slightly in the time interval which suffices to measure a few groups of measuring values in adjacent angular positions of the radiator-detector system. The correction values for the adjacent angular positions $\beta_1$ and $\beta_2$ calculated in accordance with the aforementioned method are designated $6 S \beta_1$ and $\Delta S\beta_2$. The correction value $\Delta S\beta_1 (p)$ necessary for a specific detector position p in the case of a smooth movement can be calculated by linear interpolation:

$$\Delta S \beta_1 (p) = \Delta S \beta_1 + (p - S\beta_1) \frac{\Delta S \beta_2 - \Delta S \beta_1}{p_{max}}$$

where $p_{max}$ is the maximum distance between the axis 2 and the detector position. The difference for the weighted-mean point shift $\Delta S\beta_0$ of the relevant measuring set $\beta_0$ from the initial position $p=0$ to the position $p = S\beta_1$ is thus allowed for, the difference for the weighted-mean point shift $\Delta S\beta_2$ of the next measuring set $\beta_2$ may be subsequently determined. This is valid when the measurments in the angular positions $\beta_1$ and $\beta_2$ follow each other directly in time, i.e. it is not valid for measurements in the initial position and in the end position.

It is also possible to apply other types of interpolation, for example cubic interpolation (in which case several adjoining series of measuring values are to be observed at the same time).

The different shifts of the individual measuring values of a group will cause the weighted-mean point of the functions constituted by these shifted measuring values to be shifted in most cases. It is thus possible that the new weighted-mean lines through these new weighted-mean points will not intersect at one point. In order to further improve the accuracy of the method and to obtain a further suppresion of artifacts, new weighted-mean points $S'\beta$ are determined for the functions resulting from the shifted measuring values $Q'(p,\beta)$ (and thus the perpendicular distances of the weighted-mean lines $G'\beta$), which pass through the new weighted-mean points, to an arbitrary point or to the probable weighted-mean point and by means of these new distances, the corrected or shifted measuring values are again shifted as described hereinbefore. Thus, the individual measuring values are shifted iteratively. Each iteration comprises the following steps:

(1) Calculation of the weighted-mean points $S\beta$ from the measuring values or from the measuring values already corrected $Q(p,\beta)$ for all angular positions $\beta$, (2) Calculation of the correction values $\Delta S\beta = D(G\beta, B)$, i.e. the perpendicular distance of the weighted mean line $G\beta$, which passes through the weighted mean $S\beta$, to the point B, (3) Corrective shifting of the measuring values in accordance with the value obtained from $\Delta S\beta$ by interpolation as described hereinbefore.

It is known that may iterative processes tend to yield results which become worse after a certain number of iteration steps. Therefore, such iterative processes should be discontinued after the $I^{th}$ iteration. In order to measure the result of an iterative step, the sum $\sum_\beta \Delta S\beta$ may be calculated. It should be smaller then the corresponding value of the preceding iteration, if not the iterative process should be stopped.

Figure 3:
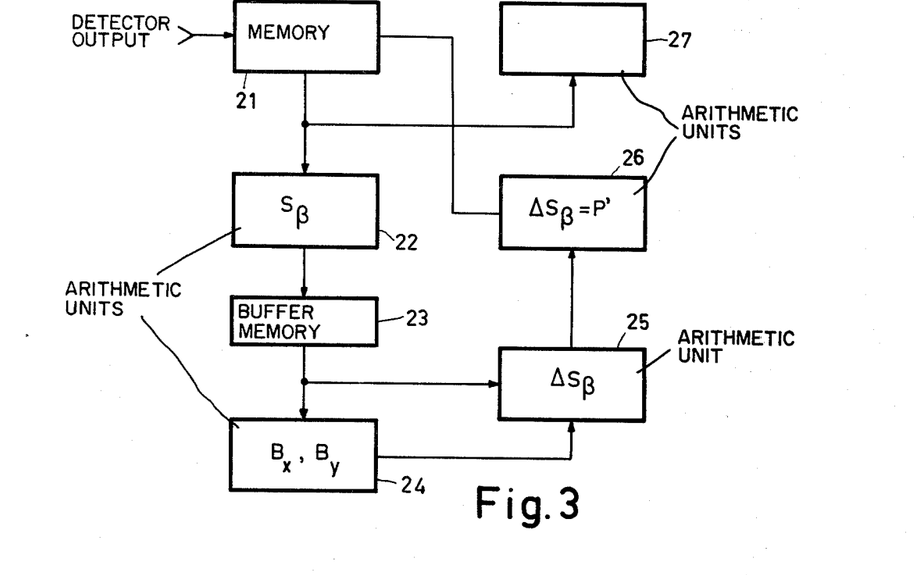
FIG. 3 is a block diagram of an arrangement in accordance with the invention.

FIG. 3 is a device for carrying out the described method. The measuring values supplied by the detector are stored in the memory 21. When scanning of the body to be measured is completed in all angular positions, the sets of measuring values corresponding to each angular position are consecutively applied to the arithmetic unit 22, which determines the coordinate value of the weighted-mean point for each group. These values are consecutively stored in the buffer memory 23. From these stored values and the values of the angular function $\sin\beta$ and $\cos\beta$, which may for example be stored permanently e.g. in a read only memory (ROM), the arithmetic unit 24 derives the coordinate values of the probable weighted-mean point.

Subsequently the values stored in the buffer 23 are consecutively read and applied to the third arithmetic unit 25, which with the aid of the constant values from the fourth arithmetic unit 24 determined such stores the distance $\Delta S\beta$ of the weighted-mean line to the probable weighted-mean point for each value read from the memory 23.

The measuring values are again read from the memory 21 and again written in an address which is determined by the fifth arithmetic unit 26 on the basis of the distance values stored in the third arithmetic unit 25 and the relevant address during read-out, so that the first arithmetic unit 27, which reconstructs the image, can directly use the series of shifted measuring values, stored in the memory 21, in accordance with their final addresses, to determine the absorption distribution in the planar slice.

The fourth arithmetic unit 24 may be dispensed with when the distances of the weighted-mean lines are not determined relative to the probable weighted-mean point, but relative to an arbitrary point, for example the origin of the coordinate system x, y in FIG. 1.

If the measuring values are to be shifted iteratively, the arithmetic unit 27 repeats the cycle of corrective computations by the arithmetic units 22, 24, 25 and 26 before the measuring values are processed.

Figure 4:
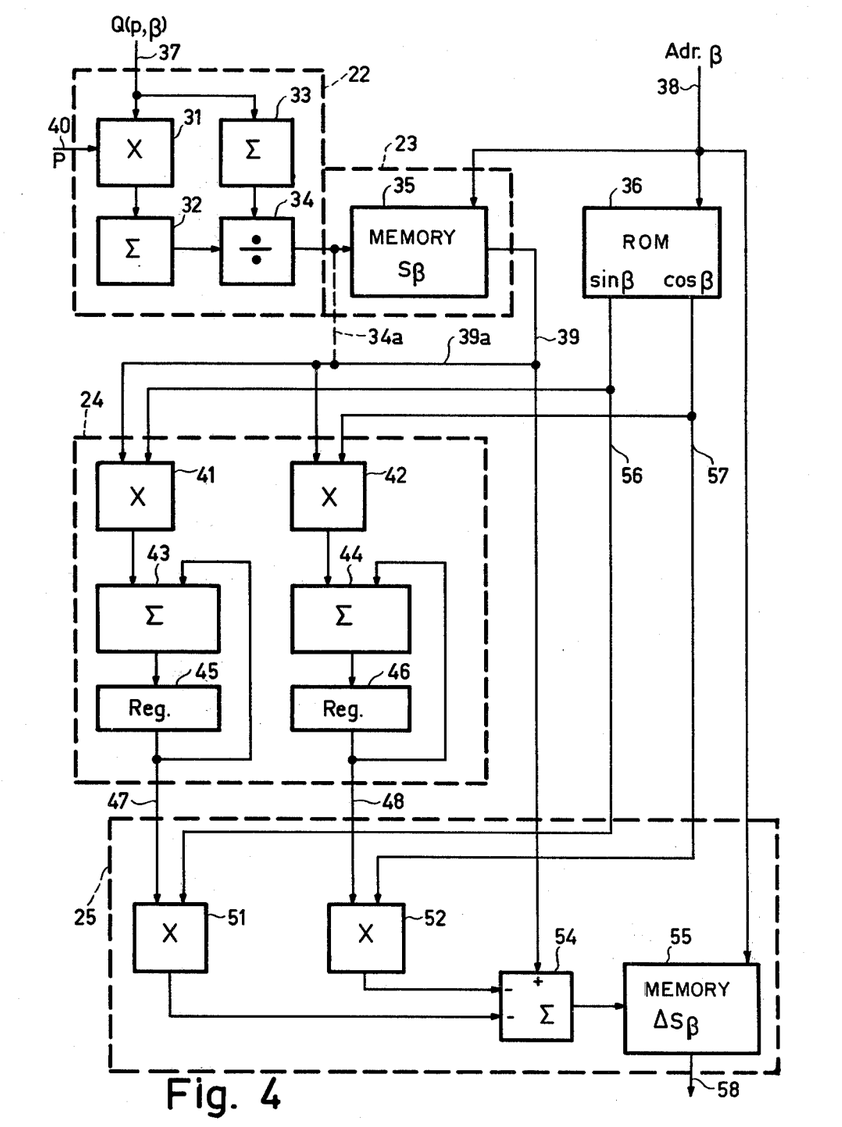
FIG. 4 shows a part of the block diagram of FIG. 3 in more detail.

FIG. 4 shows some of the arithmetic units shown in FIG. 3 in more detail. The second arithmetic unit 22 comprises an adding device 33, whose circuit design for example corresponds to that of the adding devices in the arithmetic unit 24. This adding device 33 adds the measuring values $Q(p,\beta)$ of each measuring-value series, which are applied consecutively from the memory 21 in FIG. 3 via the line 37 and applies the value of the sum total to the divider 34. Furthermore the measuring values are applied to a further adding device 32 via a multiplier 31, which multiplies each measuring value $Q(p,\beta)$ by the corresponding coordinate value p of the measuring beam which has produced the relevant measuring value, said coordinate value being applied via the input 40. Adding device 32 also adds the products of each series and applies the corresponding value of the sum total to the further input of the divider 34. The quotient of the two values applied to the divider 34 is the coordinate value for the weighted-mean point $S\beta$ of each series of measuring values, which is stored in the memory 35, which corresponds to the buffer memory 23 in FIG. 3. This memory 35 may be a shift register, which after each series of measuring values receives a shift-register clock pulse via the line 38, or it may be a random-access memory, which receives a coded address corresponding to the angular position $\beta$ via the line 38.

The coordinate values for the probable weighted-mean point of the image to be constructed are derived from these values for the weighted-mean points in the arithmetic unit 24. For this purpose the values stored in the memory 35 are applied to the multipliers 41 and 42 via the line 39 and the connection 39a, the other inputs of said multipliers receiving the corresponding values for the angular functions from the read-only memory 36 via the lines 56 and 57. The read-only memory 36 is controlled in parallel with the memory 35, via the line 38 so that the allocation of the weighted-mean points, relative to the individual angular positions and the corresponding angular functions, is necessarily guaranteed. As the arithmetic unit 24 processes the weighted-mean point values consecutively, these values may also be applied directly from the divider 34 to the multipliers 41 and 42 via the dashed connection 34a, in which case the connection 39a can be dispensed with. Thus, after all the weighted mean points have been determined, the coordinates of the probable weighted mean point are determined simultaneously, so that time is saved. These coordinate values of the probable weighted-mean points are obtained in adding devices by addition of the products of the multipliers 41 and 42, which adding devices each comprise an adder 43 and 44 respectively and a register 45 and 46 respectively. Upon each change of the values at the input of the multipliers 41 and 42, which is attended by a change of the signal or the address on the line 38, the sum of the previously formed product and the sum so far obtained, which is contained in the registers 45 and 46 respectively, is again transferred to this register. This circuit arrangement is similar to that of the accumulator-register in a computer.

When the weighted-mean points of all series of measuring values have been determined, the register 45 or 46 contains the coordinate value of the probable weighted-mean point. The registers 45 and 46 no longer receive any transfer clock pulses so that this value is preserved. These constant values are applied to the multipliers 51 and 52 in the unit 25 via the lines 47 and 48. The other inputs of the multipliers 51 and 52 consecutively receive the values of the angular functions $\sin\beta$ and $\cos\beta$ via the lines 56 and 57, and at the same time the summing device 54 consecutively receives the values of the weighted-mean points of the measuring value series for the corresponding angular positions via the line 39 and adds to said values the instantaneous products of the multipliers 51 and 52 with negative sign, i.e. substracts them. Thus, the values of the distance of the instantaneous weighted-mean lines to the probable weighted-mean point appear consecutively on the output of the adding device 54, i.e. the correction values $\Delta S\beta$ for the measuring values of the corresponding series, and these values are stored in the memory 55, which is controlled in synchronism with the memories 35 and 36 via the line 38. Subsequently these correction values are available again via the line 58 for correction of the measuring values.

If the distance values is not determined relative to the probable weighted mean point, but relative to an arbitrary point, the coordinates of the arbitrary point are applied to the multipliers 51 and 52 via the lines 47 and 48, and the arithmetic unit 24 with the elements 41 to 46 may be dispensed with.

The values for the weighted-mean distances $\Delta S\beta$ appearing on the line 58 may now be employed, during read-out of the measuring values from the memory 21 in FIG. 3, for reading these measuring values shifted by the corresponding addresses, so that they can be processed for reconstruction of the image in the arithmetic unit 27. However, as the individual measuring values are needed several times for reconstruction, it is more effective not to read the measuring values in a shifted manner upon each access operation, but rather to restore them in correspondingly shifted addresses during a preceding operation in the memory 21, so as to render the measuring values directly accessible for processing.

Figure 5:
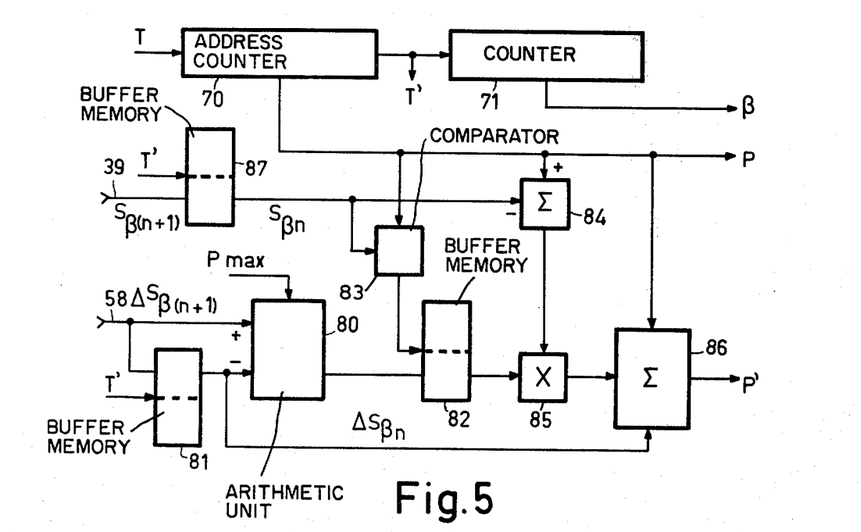

This is effected in the arithmetic unit 26, which is shown in more detail in FIG. 5.

Said unit includes a first address counter 70, whose count input receives clock pulses T from a controlled clock-pulse generator, not shown. Said counter 70 consecutively produces the addresses p of each group of measuring values at its output. The counter 70 supplies a transfer signal, after the last address referred to as auxiliary clock pulse T', which is applied to a counter 71, at whose output the addresses $\beta$ of the individual series of measuring values are available in accordance with the corresponding angular positions. These two address signals p and $\beta$ are applies both to the memory 21 in FIG. 3 and to the arithmetic unit shown in FIG. 4. Applying the group address $\beta$ via the line 38 in FIG. 4 results in the value of the weighted-mean point $S\beta$ corresponding to this series being produced on the line 39 and the value of the corresponding weighted-mean distance $\Delta S\beta$ on the line 58. These values which appear in the form of electrical signals are applied to the lines in FIG. 5 which bear the corresponding references. Upon the change from the group address $\beta_n$ to the group address $\beta(n+1)$ the value of the weighted-mean point or the weighted-mean coordinates respectively is passed to a buffer memory 87 upon the auxiliary clock pulse T' and transferred to its output, so that in this way each time the value of the weighted-mean coordinates of the preceding series appears on the output of the buffer memory 87. However, the address input of the memory 35 in FIG. 4 may instead be controlled by a preceding adder stage with a fixed shift by one address.

The value of the weighted-mean point coordinates $S_{\beta n}$ is applied with a negative sign to the one input of an adding device 84, whose other input receives the value of the measuring value addresses p with a positive sign, and at whose output the value of the address relating to the weighted-mean point coordinates is available, which is applied to an input of a multiplier 85.

The value of the weighted-mean distance $\Delta S_{\beta(n+1)}$ which appears on the line 58 in FIG. 4 is applied to an arithmetic stage 80 with positive sign and also to a second buffer memory 81, which in a similar way as the first buffer memory 87 may consist of a plurality of parallel bistable multivibrator stages. Upon each auxiliary clock pulse T' (i.e. upon each change of the group address $\beta$), the value of the instantaneous weighted-mean distance $\Delta S_{\beta n}$ is transferred to the buffer memory 81 and passed to its output, while the value of the weighted-mean distance $\Delta S_{\beta(n+1)}$ of the next series appears at the input. Thus the second buffer memory 81 also causes a shift of the weighted-mean distance by one address, while in both the direct value and the shifted value are neded simultaneously in the arithmetic unit 80, in order to form the difference between these values, as is indicated by the signs at the inputs. In the arithmetic unit 80 said difference is furthermore divided by the fixed value $p_{max}$ corresponding to the maximum coordinate or measuring value address and the resulting value is applied to a third buffer memory 82, which also may consist of a plurality of parallel bistable multivibrator stages. This buffer memory 82 then stores the value appearing at its input upon an output signal of a comparator 83, which compares the instantaneous address p with the coordinate value of the weighted-mean point $S_{\beta n}$ and produces an output signal in the case of equality. Thus, the buffer memory 82 takes over a value which corresponds to the difference of the weighted-mean distances on the corresponding side of the weighted-mean point coordinate of each series of measuring values and applies it to the other input of the multiplier 85.

The output of the multiplier 85 is connected to an input of an adding device 86, which receives the value of the instantaneous address p via a further input and the value of the weighted-mean distance $\Delta S_{\beta n}$ corresponding to the preceding group address via a third input. The output of the adding device 86 supplies the value of the address p', in which the measuring value read from the address p is to be written, in accordance with the relationship:

$$p' = p + \Delta S_{\beta n} + (p - S_{\beta n})\frac{\Delta S_{\beta(n+1)} - \Delta S_{\beta n}}{p_{max}}$$

$$= p + \Delta S_{\beta n}(p).$$

When all measuring values have thus been re-stored, they are available for direct processing by the arithmetic unit 27 in FIG. 3.

It is to be noted that the electrical signals for the individual values, for example the measuring values, the addresses, the weighted-mean coordinates, and the weighted-mean distances, are represented in the usual manner by a plurality of parallel signals on separate lines, which for the sake of simplicity are represented as a single line in the Figures. Similarly, the memories and buffer memories as well as the processing stages, such as adding devices and multipliers, which are of known design, are adapted for processing a plurality of parallel signals.

Some processing stages may also be utilized several times, in that their inputs and outputs are switched over to the corresponding signal sources or subsequent stages. In the extreme case all memories and processing stages may also be combined and realized by a computer, which is programmed to perform the indicated cycle of processing steps.

So far, only movements of the body relative to the measuring system have been discussed. However, in general the principle described herein before may be used for all translational deviations in the position of the body relative to the measuring system. It may happen in particular that the actual position of the measuring system relative to the body during the measurement deviates from that which has been assumed for reconstruction. Deviations of a few tens of millimeters may lead to visible artefacts.

What is claimed is:

1. A computed tomography device for determining the spatial distribution of the absorption of radiation in a planar slice of a body from a plurality of measuring sets, each of which represent a series of measuring values which correspond to an integral of the absorption of the body along one of a multiplicity of at least substantially parallel measuring beams, in which the various measuring sets are derived from measuring values obtained with the aid of measuring beams which are differently oriented relative to each other within the planar slice and the spatial distribution of the absorption is derived from the sets of measuring values by superposition, of the type comprising a radiator for generating a beam of a body penetrating radiation and one or a plurality of detectors for measuring the radiation passing through the planar slice of the body, the measurements being performed with radiation passing at different orientations through the planar slice of the body, the direction of the radiation being in the plane of said slice; a memory of storing the series of measuring values; and a first arithmetic unit for determining the spatial absorption distribution in the planar slice by superposition; and further comprising, as an improvement:

second arithmetic unit means connected to the memory, which functions to calculate the coordinates of a weighted-mean point $(S,\beta)$ for each series of measuring values $(Q(p,\beta))$ measured with at least substantially the same orientation in accordance with the relationship $$S\beta = \frac{\sum_p p \cdot Q(p,\beta)}{\sum_p Q(p,\beta)};$$

a weighted-mean memory for storing the weighted-mean points;

third arithmetic unit means which function to calculate the value of the perpendicular weighted-mean distance (D(Gβ,B)) from the line through the weighted-mean point to the coordinates ($B_x$, $B_y$) of a fixed point (B), for each weighted-mean point, using in accordance with the relationship $$\Delta S\beta = S\beta + B_x \sin\beta - B_y \cos\beta; \text{ and}$$

a distance memory for storing the weighted-mean distances;

the first arithmetic unit being connected to determine the distribution of absorption in the planar slice using the measuring values of measuring series shifted by the associated weighted-mean distance.

2. A device as claimed in claim 1, further comprising fourth arithmetic unit means which functions to calculate the coordinates ($B'_x$, $B'_y$) of a probable weighted-mean point CB') of the body from the values of the coordinates of the weighted-mean line (Sβ) of the measuring sets; and an auxiliary memory connected to store said coordinates and wherein that the third arithmetic unit means functions to calculate the values for the perpendicular distance (D(GβB)) from the weighted-mean lines (Gβ) to the coordinates of the probable weighted-mean point of the body.

3. A device as claimed in claim 2, further comprising:

fifth arithmetic unit means which function to read the measuring values (Q(p,β)) of each series from the memory (21) and write each measuring value into a new address (p') of the memory in a shifted manner, said new address being calculated from on the value of the address (p) which has been read as well as on the distance $\Delta S\beta_1$ of the weighted-mean point ($S\beta_1$) of the series and the distance ($\Delta S\beta_2$) of the weighted-mean point ($S\beta_2$) of the directly adjoining series by interpolation;

and wherein that the first arithmetic unit directly uses the written measuring values in accordance with the new addresses in which said written measuring values are stored to determine the absorption distribution.

* * * * *

UNITED STATES PATENT AND TRADEMARK OFFICE
CERTIFICATE OF CORRECTION

PATENT NO. : 4,144,569
DATED : March 13, 1979
INVENTOR(S) : WOLFGANG WAGNER

It is certified that error appears in the above-identified patent and that said Letters Patent are hereby corrected as shown below:

Claim 1, line 20, "of" (first occurrence) should be --for--

Claim 2, line 4, "CB')" should be --(B')--

Signed and Sealed this

Ninth Day of October 1979

[SEAL]

Attest:

RUTH C. MASON
Attesting Officer

LUTRELLE F. PARKER
Acting Commissioner of Patents and Trademarks